(12) United States Patent
Jaunsem

(10) Patent No.: US 6,300,546 B1
(45) Date of Patent: Oct. 9, 2001

(54) SMALL WHITE PUMPKIN; PLANTS, TISSUE, AND SEEDS FOR PRODUCING THE PUMPKIN; AND THE METHODS FOR GROWING THE PLANTS

(76) Inventor: John Jaunsem, R.D. 3 Box 347, Middleburg, PA (US) 17842

( * ) Notice: Subject to any disclaimer, the term of this patent is extended or adjusted under 35 U.S.C. 154(b) by 0 days.

(21) Appl. No.: 07/773,846

(22) Filed: Oct. 11, 1991

(51) Int. Cl.[7] .............................. A01H 5/00; A01H 11/00; A01H 1/00
(52) U.S. Cl. ......................... 800/310; 800/260; 800/295
(58) Field of Search .................................. 800/200, 255, 800/DIG. 20; 47/58, DIG. 1

(56) References Cited

PUBLICATIONS

Burpee & Co., Burpee Seed Catalog, Spring 1989, p. 141, Copyright 1988, W. A. Atlee Burpee & Co. 300 Park Ave., Warminster PA 18974.*

Heiser, C. B., *The Gourd Book,* Norman, OK, Univ. of Oklahoma Press, 1979, pp. 38–47, Esp. pp. 43–44.*
Warrick, J. B., Los Angeles Times, Oct. 26, 1986, (Sunday) Section 1, p. 2, Part 1, col. 2.*
Lemke, C., et al., Hort Science, vol. 14 (1979) p. 39.*
J. Amer. Soc. Hort. Sci. 104(5):674–677. 1979, The Use of Ethephon to Regulate Sex Squash for Hybrid Seed Production, S. Shannon and R.W. Robinson.

* cited by examiner

*Primary Examiner*—Bruce R. Campell
*Assistant Examiner*—Ram R. Shukla
(74) *Attorney, Agent, or Firm*—Peter K. Trzyna, Esq.

(57) ABSTRACT

The present invention relates to a multi-cellular organism and parts thereof and a method for growing the same. More particularly, the present invention relates to small white pumpkins, plants that produce the pumpkins, seeds and tissue that produce the plants, and a method for growing the small white pumpkins to further reduce the size of the pumpkins.

22 Claims, 1 Drawing Sheet

(1 of 1 Drawing Sheet(s) Filed in Color)

SMALL WHITE PUMPKIN; PLANTS, TISSUE, AND SEEDS FOR PRODUCING THE PUMPKIN; AND THE METHODS FOR GROWING THE PLANTS

BACKGROUND OF THE INVENTION

1. Field of the Invention

The present invention relates to a multi-cellular organism and parts thereof and a method for growing the same. More particularly, the present invention relates to small white pumpkins, plants that produce the pumpkins, seeds and tissue that produce the plants, and a method for growing the small white pumpkins to further reduce the size of the pumpkins.

2. Description of the Related Art

There is an ever present need for plant diversity, and this need manifests itself in many ways. Among these is the commercial demand for new ornamental plants and parts thereof and for new and interesting food crops.

This need is addressed through the creation and discovery of new plants. For example, new plants are developed from sport (a nonsexual variation of a plant) or from mutations (a sexual or nonsexual variation of a species). Also, new plants are discovered from time-to-time, and genetic engineering has been used to create new plants.

Plant growing techniques have also evolved to add to the diversity of life. Some of these techniques involve the use of plant growth regulants, usually to increase plant growth.

With regard to the Cucurbitaceae family, the demand for plant diversity has resulted in the development of small pumpkins. According to a search conducted by the U.S. Department of Agriculture Office of Plant Variety Protection of the PVSQUA Database for gourds, pumpkins, and squash, the Munchkin variety (Database Ref. No. 8710001) discovered by Moran and introduced in 1987 is a small orange pumpkin. This summer pepo species reportedly has a length of 9 cm and a fruit stem end width of 9 cm. The fruit shape is known as "Connecticut Field" with a prominent presence of "ribs."

Another small orange pumpkin is the Jack-Be-Little variety (Database Ref. No. 8510020) originated by Le Marche Seeds International and introduced in 1985. Also a summer pepo, Jack-Be-Little is somewhat smaller than Munchkin. Jack-Be-Little reportedly has a fruit length of 5 cm, a fruit stem end width of 7 cm, and a fruit blossom end width of 7 cm. According to the U.S. Plant Variety Protection Office, the average weight of the fruit is 110 grams. The shape is again the Connecticut Field type, with a prominent presence of ribs. The surface texture is described as smooth (i.e., no warts).

There have also been white, cream, or buff colored pumpkins. The PVSQUA database lists several C. moschata varieties with this coloration, including Allneck Cushaw (Database Ref. No. 7610116), Calhoun (Database Ref. No. 7610231), Cheese (Database Ref. No. 7610234), Golden Cushaw (Database Ref. No. 7610236), Green Striped Cushaw (Database Ref. No. 7610237), Quaker Pie (Database Ref. No. 7610241), and Virginia Mammoth (Database Ref. No. 7610244).

The PVSQUA database also lists several *Cucurbita pepo* varieties with this coloration, including Custard (Database Ref. No. 7610190), which is described as a summer pumpkin. The description suggests that a banana-shaped fruit of a cream/white color grows in vines.

Another *Cucurbita pepo* variety of this coloration is Little Boo (Database Ref. No. 7800057), reportedly originated by Agway Inc. and introduced in 1978. It is said that this winter pumpkin is a vine plant producing Connecticut Field-shaped fruit colored white. According to the U.S. Plant Variety Protection Office, the pumpkins weigh about 3,160 gm.

There also is a report of a White Bush Scallop (Database Ref. No. 7610225), an early white bush scallop, Cucurbita pepo. The description is that this summer squash has white scalloped fruit.

A White Perr Gourd (Database Ref. No. 7610058) is mentioned as a *Cucurbita pepo* variety that produces white fruit on a vine.

Finally, according to Database Ref. No. 8600093, a *Cucurbita pepo* variety called "Happy" was originated by Jennie Brush and introduced in 1986 Happy is described as a summer squash of mixed species having a bush plant habit. The fruit is characterized as Connecticut Field-shaped colored white. The U.S. Plant Variety Protection Office indicates that the fruit weighs about 4,536 gm.

In addition, prior to Oct. 11, 1990, the inventor observed a roadside stand selling small, lemon-yellow pumpkins in Sunbury, Pa. A person attending the stand stated that these pumpkins resulted from a planting of Jack-Be-Little seeds.

However, so far as is presently known, prior to the present invention, a pumpkin of the approximate size of Munchkin or Jack-Be-Little has not been produced in a pure white color.

SUMMARY OF THE INVENTION

It is an object of the present invention to provide a new pumpkin.

It is a further object of the present invention to provide a new pumpkin characterized by its whitish color and its diminutive size.

It is another object to provide plants, tissue, and seeds for growing the plants.

It is still another object of the present invention to provide methods for growing the plants, including a method to produce an even smaller pumpkin and a method to produce new varieties.

These and other objects are addressed by pumpkins, which are small and white, plants and tissue that produce the pumpkins, and seeds that produce the plants, tissue, and pumpkins. Methods for growing the pumpkins are also provided.

"The file of this patent contains at least one drawing executed in color. Copies of this patent with color drawings will be provided by the Patent and Trademark Office upon request and payment of necessary fee."

DETAILED DESCRIPTION OF THE INVENTION

Figure 1:
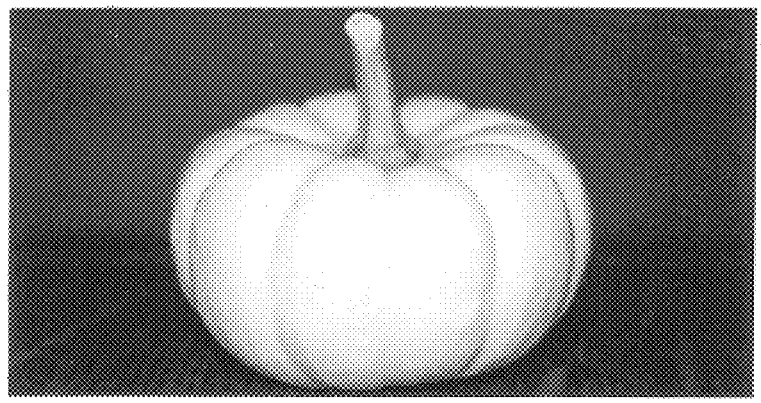
FIG. 1 is a photograph of the pumpkin of the present invention.
Figure 2:
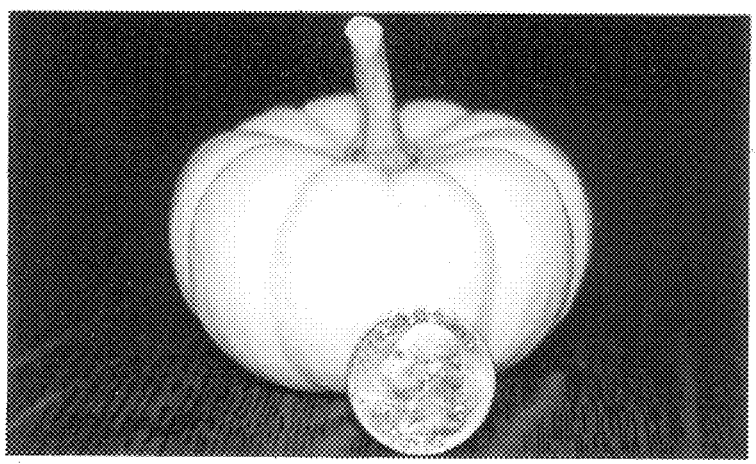
FIG. 2 is another photograph of a pumpkin of the present invention.
Figure 3:
FIG. 3 is a photograph of the pumpkin plant of the present invention, the pumpkin being shown in comparison of its size to that of a quarter.

The present invention includes a pumpkin variety Cucurbita pepo BABY BOO that is the subject of an application by the inventor herein for a plant variety protection certificate, PVP #9100011, filed with the U.S. Plant Variety Protection Office on Oct. 11, 1990. Irrespective of plant varieties, however, the present invention includes small white pumpkins. For ornamental purposes, these pumpkins are preferably as small and as white as possible. For example, pumpkins less than 150 grams are preferable, or better yet, below 100 grams, or even below 50 grams. These pumpkins can be produced, for example, by plants that produced the seed that has filed with the American Type Culture Collection, 12301 Parklawn Drive, Rockville, Md. 20852 (U.S.A.), pursuant to 37 C.F.R. §§ 1.801 et seq. The deposit account number is 75121.

In 1985, the inventor herein discovered one white pumpkin in his planted patch of small orange pumpkins, probably of the Jack-Be-Little variety. The patch of pumpkins came from seeds of fruit purchased in 1984 at a produce terminal in Georgia. Accordingly, the small white pumpkin is believed to be the result of a mutation or a sport.

In 1986, a portion of the seeds from the one small white pumpkin were planted and open-pollinated. After a drought occurred, one vine survived to produce three small white pumpkins. Those pumpkins were collected.

In 1987, the seeds remaining from the original 1985 small white pumpkin were planted along with seeds from the three 1986 white pumpkins. The result was many plants that were thinned to 50 plants. These plants were blind hand-pollinated, and 5 of these plants produced white pumpkins.

In 1988, ten plants were grown from seeds of each of the five plants the previous year. Two lines (88 A and 88 B) produced small white pumpkins. The diameter of the white pumpkins ranged from about 2½ inches to about 4 inches, with the average being about 3⅛ inches.

In 1989, the inventor selected seeds from the plant that produced the whitest fruit from each of lines 88 A and 88 B. Fifteen seedlings of each of these lines were planted to produce lines 89 A and 89 B.

In 1990 seeds from 13 lines from 89 A that produced the whitest pumpkins were planted. Also, FLOREL was used to inhibit stamen development. (FLOREL is a product commercially available in the United States that is distributed by Southern Agricultural Insecticides, Inc., Boone N.C.) The fruit from those plants are summarized in Table 1 below.

TABLE 1

| 1990 Lines | Color | Number of Plants |
|---|---|---|
| 1 | 100% white | 42 |
| 2 | 100% white | 35 |
| 3 | 100% white | 35 |
| 4 | 100% white | 33 |
| 5 | 100% white | 69 |
| 6 | 100% white | 101 |
| 7 | 63% white | 35 |
| 8 | 71% white | 35 |
| 9 | 63% white | 35 |
| 10 | 89% white | 34 |
| 11 | 100% white | 35 |
| 12 Mtyp | 100% white | 28 |
| 13 Ofc | 100% white | 32 |

With the exception of lines 7–10, all pumpkins were white. (In Table 1, "Ofc" refers to pumpkins of one plant that were white, but somewhat off-color.) Thus, from the data in Table 1, it can be seen that the characteristic of producing small white pumpkins is now stable and genetically transmitted to progeny.

The 1991 seedlings also produced three shapes of fruit. One shape is a rounded pyramidal or a rounded conical shape. A second shape is "Mtyp," or medium-type, having a height about equal to the width. The third shape is the Connecticut Field type as shown in FIG. 1. The shapes of the Connecticut Field type and the Mtyp tend to be so indented in the top of the fruit that the top collects rain water.

In 1991, hand-pollinated seeds of lines 1–6 of 89 A were raised. Of 2,050 seeds, there was about a 92% rate of germination in Hall, New York. The plants produced only small white pumpkins, a sample of which had the following approximate characteristics set forth in the tables below. Table 2 is directed to the size of the pumpkins and Table 3 is directed to the whiteness of the pumpkins.

TABLE 2

| Line No. | No. of Fruit | Weight Range (Grams) | Diameter In Inches | Height In Inches |
|---|---|---|---|---|
| H 1 | 19 | 112–275 | 2¹¹⁄₁₆–3¹¹⁄₁₆ | 1⁹⁄₁₆–2²⁄₁₆ |
| H 2 | 4 | 246–289 | 3⁹⁄₁₆–3¹¹⁄₁₆ | 2⁴⁄₁₆–2⁵⁄₁₆ |
| H 3 | 17 | 200–492 | 3³⁄₁₆–4⁴⁄₁₆ | 2⁶⁄₁₆–2¹⁵⁄₁₆ |
| H 4 | 16 | 140–229 | 2¹⁴⁄₁₆–3¹⁴⁄₁₆ | 1⁹⁄₁₆–1¹⁵⁄₁₆ |
| H 5 | 22 | 140–241 | 2¹³⁄₁₆–3¹⁰⁄₁₆ | 1¹⁰⁄₁₆–1¹⁵⁄₁₆ |
| H 6 | 22 | 146–251 | 2¹⁴⁄₁₆–3¹¹⁄₁₆ | 1¹¹⁄₁₆–2 |

The fruit harvested in Hall, N.Y. (the H Lines) though random, may be slightly prejudiced toward large sized pumpkins. Only hand-pollinated fruit were harvested (the hand-pollinations began on or about Jul. 24, 1991). Thus, these pumpkins were on the vine longer than the general population of the pumpkins in the field. Lines 1 and 4–6 were predominately Connecticut Field shaped, while the remainder were m,typ.

Coloration data is shown in Table 3. The colors are determined with reference to fan 4 (unless another fan is mentioned) of The Royal Horticultural Society Colour Chart (in Association with the Flower Council of Holland, published in London and in Leiden).

TABLE 3

| Lines | Date Seeded | Date Harvested | Days Growing Before Harvest | Days Off Vine Until Color Test |
|---|---|---|---|---|
| 6J 1 | 4/24 | 8/5 | 103 | 63 |
| 6J 2 | 4/24 | 8/5 | 103 | 63 |
| PA6 A | 5/6 | 10/9 | 156 | 1 |
| PA6 B | 5/6 | 10/9 | 156 | 1 |
| PA6 C | 5/6 | 10/9 | 156 | 1 |
| PA6 D | 5/6 | 10/9 | 156 | 1 |
| 1F | 6/1 | 9/18 | 109 | 22 |
| 5F | 6/7 | 10/2 | 117 | 8 |
| H 1 | 5/26 | 9/27 | 124 | 13 |
| H 2 | 5/26 | 9/27 | 124 | 13 |
| H 3 | 5/26 | 9/27 | 124 | 13 |
| H 4 | 5/26 | 9/27 | 124 | 13 |
| H 5 | 5/26 | 9/27 | 124 | 13 |
| H 6 | 5/26 | 9/27 | 124 | 13 |

| | # of Fruit | # of Plants | Color Range Light | Color Range Dark | Date Color Determined |
|---|---|---|---|---|---|
| 6J 1 | 1 | 1 | 158D | | 10/10/91 |
| 6J 2 | 1 | 1 | 158C | | 10/10/91 |
| PA6 A | 10 | 1 | 158B | 158A | 10/10/91 |
| PA6 B | 10 | 1 | 158B | 158A | 10/10/91 |
| PA6 C | 10 | 1 | 158B | 158A | 10/10/91 |
| PA6 D | 10 | 1 | 158B | 158A | 10/10/91 |
| 1F | 30 | 30 | 159D | 158B | 10/10/91 |

TABLE 3-continued

| 5F | 30 | 30 | 158C | 158B | 10/10/91 |
|---|---|---|---|---|---|
| H 1 | 19 | 19 | 158C | 158B | 10/10/91 |
| H 2 | 4 | 4 | 158B | 158A | 10/10/91 |
| H 3 | 17 | 17 | 159D | 158B | 10/10/91 |
| H 4 | 16 | 16 | 158B | 158A | 10/10/91 |
| H 5 | 22 | 22 | 158B | 158A | 10/10/91 |
| H 6 | 22 | 22 | 158B | 158A | 10/10/91 |

The results of the color chart data in Table 3, Lines 6J 1 and 6J 2, also suggest that by picking the fruit at the proper time, the whitest fruit is obtained, and the fruit stays the whitest the longest. Since 6J 1 and 6J 2 were grown in the first part of the growing season, it is reasonable to conclude that they were grown with less thermal units (growing degree days) than say, Line 1F and, indeed, all the other pumpkin groups. Therefore, in terms of thermal units, the fruit from lines 6J 1 and 6J 2 were on the vine considerably less than any of the other pumpkin groups.

The lines of pumpkins grown in Hall, NY (H 1, H 2, H 3, H 4, H 5, and H 6) contain pumpkins as light as pumpkins from plants treated with FLOREL in lines 1 F, 5 F, and PA6A–D, but show the pumpkins contain a higher range of darker tones (158A is darker than 158B). Lines PA6 (A–D) contain ten pumpkins each from four different plants. This group shows that by remaining on the vine for 156 days, the darkest readings were observed. Thus, to obtain the whitest pumpkins, the pumpkins must be harvested at maturity and not left on the vine to overripen.

A comparison of lines 1 F and 5 F versus lines 6J 1 and 6J 2 suggests that FLOREL has no effect on whiteness.

Yellowing, streaks, blotches, or spots can occur on fruit of any plant and seem to occur under stress. If these conditions exist for a given plant, they have been observed to appear before and/or after perfectly normal white fruit development. There has been no observed plant that had all its fruit affected, except for a plant which dies. The stress can be environmental, for example, drought, disease, insect damage, or some combination of the above. If the stress is relieved, the plant resumes producing white fruit.

In addition, to the above, some sun scalding has been observed. No measurable data has been collected on scalding because the yellowing caused by the scalding has been negligible.

Also, if very immature fruit is harvested, it has a tendency to yellow. This condition is more prevalent but the entire yellow problem is minor considering the amount of fruit per plant.

With regard to growing plants from seeds to produce the small white pumpkins, approximately 10 days after seed germination, a cotyledon forms to a size of about 31 mm long and 22 mm wide. The length of the entire stem and leaf is about 37 mm long.

Thereafter, the plants produce vines, as contracted with bush or semi-bush plants. The vines tend to be prickly rather than pilose or glabrous. The plant has a main stem that is generally round but has small ridges along its length. The vines are about 13 mm in diameter at the midpoint of the first internode and have an average length of about 77 cm, ranging from about 1 foot 6¼ inches to about 3 feet 9 inches. The number of internodes varies from about 8 to 48, and the length of the internodes tends to range from about 2.5 cm to about 12.7 cm.

Leaves emanate from the vines. The leaves are about 25 cm wide and 23 cm long. The apex of the leaves is rounded, and veining is plainly visible. The leaves have a dorsal surface that is a dark green and a ventral surface that is a lighter green. The leaves are not blotched. The dorsal and ventral surfaces are soft and hairy. The petiole length is about 25 cm.

Flowers also emanate from the vines. The flowers are generally yellowish orange in color. The flowers have an open flower diameter at maturity of about 13.7 to 15 cm. The flowers have a straight, plain margin, and flower sepals are about 2–3 mm in width, ranging in length from about 25 to about 40 mm. The flowers each produce an ovary that is not turbinate or fusiform, and the pedicel has a length of about 0.9 cm.

Stalks also emanate from the vines. The stalks have dimensions of about 2–4 cm in length and a diameter of about 0.6 cm, with an expanded end for attaching to the fruit (i.e., pumpkins). However, the fruit detaches easily from the vines.

The plants produce about 15–30 pumpkins about 90 days after germination. The pumpkins have a white flesh with a fine, firm texture that is moist and edible. The flesh ranges from about 9–11 mm at the top of the pumpkin to about 7–9 mm along the side and bottom of the pumpkin. The flesh of the pumpkin is protected by a hard rind.

The pumpkins have a seed cavity of about 3.7 cm in length and about 6 cm in width. The seed cavity generally conforms to the shape of the pumpkins. There is abundant placental tissue and a prominent center core in the seed cavity.

The plant pumpkins each produce about 150 normal seeds. The seeds are about 10 m in length, 5 mm in width, and 2 mm in thickness. The seeds are cream to white and semi-glossy with a straight, rounded margin. The seeds are moderately easy to separate from pulp in the seed cavity.

The plants of the present invention can be used to cross-pollinate other members of the Cucurbitaceae family to produce new varieties. For example, a method for creating a new variety includes taking pollen from a flower of the plant of the present invention and pollinating another member of the Cucurbitaceae family. Alternatively, the plant of the present invention can be pollination with pollen from the flower of another member of the Cucurbitaceae family. In any case, the cross-pollination can produce fruit having seeds for a new variety of plant, which will result from germinating the plant. Preferably, this method includes cross-pollinating the plant of the present invention with a *Cucurbita pepo* plant to produce a new variety of *Cucurbita pepo*.

The inventor herein has also discovered a method of growing the pumpkins to produce even smaller fruit. The method includes applying FLOREL to the plants. Florel has Ethephon (2-chloroethyl) phosphoric acid as an active ingredient, and this ingredient is believed to further reduce the size of the fruit of the present invention, as illustrated in Table 4.

TABLE 4

FloReL Applied

| | Diameter in Inches | Height in Inches | Weight in Grams |
|---|---|---|---|
| 5F | | | |
| 1. | 2¹⁴⁄₁₆ | 1¹⁰⁄₁₆ | 136 |
| 2. | 2¹¹⁄₁₆ | 1⁹⁄₁₆ | 114 |
| 3. | 2¹⁰⁄₁₆ | 1⁷⁄₁₆ | 109 |
| 4. | 2¹²⁄₁₆ | 1⁹⁄₁₆ | 117 |
| 5. | 2¹²⁄₁₆ | 1¹²⁄₁₆ | 130 |
| 6. | 2¹⁵⁄₁₆ | 1¹³⁄₁₆ | 153 |
| 7. | 2¹⁴⁄₁₆ | 1¹¹⁄₁₆ | 148 |
| 8. | 2¹³⁄₁₆ | 1¹¹⁄₁₆ | 140 |
| 9. | 2¹³⁄₁₆ | 1¹¹⁄₁₆ | 129 |
| 10. | 2¹²⁄₁₆ | 1¹³⁄₁₆ | 132 |
| 11. | 2⁸⁄₁₆ | 1⁸⁄₁₆ | 101 |
| 12. | 2⁹⁄₁₆ | 1⁸⁄₁₆ | 98 |
| 13. | 2⁸⁄₁₆ | 1¹⁰⁄₁₆ | 90 |
| 14. | 2⁹⁄₁₆ | 1¹⁰⁄₁₆ | 101 |
| 15. | 2⁸⁄₁₆ | 1¹⁰⁄₁₆ | 107 |
| 16. | 2⁸⁄₁₆ | 1⁹⁄₁₆ | 94 |
| 17. | 2⁸⁄₁₆ | 1¹⁰⁄₁₆ | 104 |
| 18. | 2⁸⁄₁₆ | 1⁹⁄₁₆ | 100 |
| 19. | 2⁷⁄₁₆ | 1¹⁰⁄₁₆ | 98 |
| 20. | 2⁷⁄₁₆ | 1⁸⁄₁₆ | 89 |
| 21. | 2⁷⁄₁₆ | 1⁹⁄₁₆ | 92 |
| 22. | 2⁹⁄₁₆ | 1¹⁰⁄₁₆ | 106 |
| 23. | 2⁶⁄₁₆ | 1¹¹⁄₁₆ | 94 |
| 24. | 2⁷⁄₁₆ | 1⁷⁄₁₆ | 87 |
| 25. | 2⁷⁄₁₆ | 1⁹⁄₁₆ | 91 |
| 26. | 2⁷⁄₁₆ | 1¹⁰⁄₁₆ | 97 |
| 27. | 2³⁄₁₆ | 1⁸⁄₁₆ | 76 |
| 28. | 2⁵⁄₁₆ | 1⁷⁄₁₆ | 73 |
| 29. | 2⁴⁄₁₆ | 1⁷⁄₁₆ | 69 |
| 30. | 1¹⁵⁄₁₆ | 1³⁄₁₆ | 40 |
| 1F | | | |
| 1. | 2¹⁵⁄₁₆ | 1¹¹⁄₁₆ | 137 |
| 2. | 2¹⁵⁄₁₆ | 1¹⁴⁄₁₆ | 146 |
| 3. | 2¹²⁄₁₆ | 1¹²⁄₁₆ | 121 |
| 4. | 2¹⁴⁄₁₆ | 1¹²⁄₁₆ | 126 |
| 5. | 2¹¹⁄₁₆ | 1¹⁰⁄₁₆ | 113 |
| 6. | 2¹¹⁄₁₆ | 1⁹⁄₁₆ | 105 |
| 7. | 2¹²⁄₁₆ | 1⁹⁄₁₆ | 103 |
| 8. | 2¹⁰⁄₁₆ | 1¹²⁄₁₆ | 113 |
| 9. | 2⁹⁄₁₆ | 1⁹⁄₁₆ | 97 |
| 10. | 2¹⁰⁄₁₆ | 1⁹⁄₁₆ | 101 |
| 11. | 2¹⁰⁄₁₆ | 1⁸⁄₁₆ | 91 |
| 12. | 2⁸⁄₁₆ | 1⁸⁄₁₆ | 91 |
| 13. | 2¹³⁄₁₆ | 1⁸⁄₁₆ | 98 |
| 14. | 2⁸⁄₁₆ | 1¹²⁄₁₆ | 99 |
| 15. | 2⁹⁄₁₆ | 1⁸⁄₁₆ | 89 |
| 16. | 2⁸⁄₁₆ | 1⁹⁄₁₆ | 89 |
| 17. | 2⁷⁄₁₆ | 1⁹⁄₁₆ | 83 |
| 18. | 2⁷⁄₁₆ | 1⁹⁄₁₆ | 81 |
| 19. | 2⁴⁄₁₆ | 1⁸⁄₁₆ | 80 |
| 20. | 2⁵⁄₁₆ | 1⁹⁄₁₆ | 82 |
| 21. | 2⁸⁄₁₆ | 1⁹⁄₁₆ | 89 |
| 22. | 2⁷⁄₁₆ | 1⁹⁄₁₆ | 64 |
| 23. | 2⁵⁄₁₆ | 1⁹⁄₁₆ | 69 |
| 24. | 2⁵⁄₁₆ | 1⁷⁄₁₆ | 77 |
| 25. | 2⁴⁄₁₆ | 1⁹⁄₁₆ | 61 |
| 26. | 2³⁄₁₆ | 1⁷⁄₁₆ | 64 |
| 27. | 2⁴⁄₁₆ | 1⁶⁄₁₆ | 59 |
| 22. | 2²⁄₁₆ | 1⁶⁄₁₆ | 54 |
| 29. | 2³⁄₁₆ | 1⁴⁄₁₆ | 49 |
| 30. | 1¹⁵⁄₁₆ | 1³⁄₁₆ | 41 |

FloReL Not Applied

| | Diameter in Inches | Height in Inches | Weight in grams |
|---|---|---|---|
| PA6 A | | | |
| 1. | 3⁷⁄₁₆ | 2 | 227 |
| 2. | 3⁶⁄₁₆ | 2²⁄₁₆ | 215 |
| 3. | 3⁵⁄₁₆ | 1¹⁵⁄₁₆ | 190 |
| 4. | 3³⁄₁₆ | 1¹²⁄₁₆ | 170 |
| 5. | 3²⁄₁₆ | 1¹²⁄₁₆ | 148 |
| 6. | 2¹³⁄₁₆ | 1¹²⁄₁₆ | 129 |
| 7. | 2¹⁵⁄₁₆ | 1¹⁰⁄₁₆ | 128 |
| 8. | 2¹³⁄₁₅ | 1¹¹⁄₁₆ | 118 |
| 9. | 2¹⁰⁄₁₆ | 1⁸⁄₁₆ | 100 |
| 10. | 2⁹⁄₁₆ | 1¹⁰⁄₁₆ | 101 |
| PA6 B | | | |
| 1. | 3²⁄₁₆ | 1¹³⁄₁₆ | 163 |
| 2. | 3⁷⁄₁₆ | 1¹⁴⁄₁₆ | 212 |
| 3. | 3³⁄₁₆ | 1¹²⁄₁₆ | 177 |
| 4. | 3⁷⁄₁₆ | 1¹⁴⁄₁₆ | 192 |
| 5. | 3 | 1¹⁰⁄₁₆ | 130 |
| 6. | 3⁷⁄₁₆ | 1¹³⁄₁₃ | 193 |
| 7. | 3⁷⁄₁₆ | 2¹⁄₁₆ | 220 |
| 8. | 3 | 1¹³⁄₁₆ | 151 |
| 9. | 3¹⁄₁₆ | 1¹³⁄₁₆ | 146 |
| 10. | 2¹²⁄₁₆ | 1¹¹⁄₁₆ | 105 |
| PA6 C | | | |
| 1. | 3⁷⁄₁₆ | 2 | 200 |
| 2. | 3¹⁰⁄₁₆ | 2 | 258 |
| 3. | 3⁸⁄₁₆ | 1¹⁴⁄₁₆ | 210 |
| 4. | 3⁹⁄₁₆ | 1¹²⁄₁₄ | 198 |
| 5. | 3⁶⁄₁₆ | 1¹⁴⁄₁₆ | 190 |
| 6. | 3³⁄₁₆ | 1¹³⁄₁₆ | 171 |
| 7. | 3⁶⁄₁₆ | 1¹⁴⁄₁₆ | 184 |
| 8. | 3³⁄₁₆ | 1¹²⁄₁₆ | 155 |
| 9. | 3 | 1¹³⁄₁₆ | 146 |
| 10. | 3 | 1¹¹⁄₁₆ | 131 |
| PA6 D | | | |
| 1. | 3⁸⁄₁₆ | 1¹⁵⁄₁₆ | 215 |
| 2. | 3¹⁰⁄₁₆ | 2²⁄₁₆ | 274 |
| 3. | 3⁹⁄₁₆ | 1¹⁴⁄₁₆ | 230 |
| 4. | 2¹¹⁄₁₆ | 1¹⁵⁄₁₆ | 164 |
| 5. | 3⁴⁄₁₆ | 1¹⁴⁄₁₆ | 177 |
| 6. | 3¹⁄₁₆ | 1¹²⁄₁₆ | 153 |
| 7. | 2¹⁴⁄₁₆ | 1¹²⁄₁₆ | 139 |
| 8. | 2¹⁴⁄₁₆ | 1¹²⁄₁₆ | 132 |
| 9. | 2¹⁴⁄₁₆ | 1¹¹⁄₁₆ | 135 |
| 10. | 2¹⁴⁄₁₆ | 1¹²⁄₁₆ | 132 |

The plants grown in 1990 and 1991 (lines F1 and F5), which were treated with FLOREL, were sprayed in the following manner at a concentration of 450–550 parts per million: First an application was given to the plants at the two leaf stage, then again seven days later. Spraying continued on a 7–10 day schedule until about three weeks before the average first frost date. The data from lines 1F and 5F (and subsequently discussed September 1990 pumpkins) shown in Table 4 demonstrates that FLOREL consistently reduces the size and weight of the pumpkins.

Of the non-FLOREL pumpkins, the smallest diameter was 2⁹⁄₁₆ inches, the largest was 3¹⁰⁄₁₆ inches, and average was about 3¹⁄₁₆ inches; the height ranged from 1⁸⁄₁₆ inches to 2²⁄₁₆ inches, with the average being about 1³⁄₁₆ inches; and the weight ranged from 100 grams to 274 grams, with the average being about 170 grams. Of the FLOREL pumpkins, the smallest diameter was 1¹⁵⁄₁₆ inches, the largest was 2¹⁵⁄₁₆ inches, and average was about 2⁵⁄₁₆ inches; the height ranged from 1³⁄₁₆ inches to 1¹⁴⁄₁₆ inches, with the average being about 1⁹⁄₁₆ inches; and the weight ranged from 40 grams to 153 grams, with the average being about 96 grams. Accordingly, the data suggests that the application of FLOREL to the plants further reduces the size of the pumpkins.

This inference is also supported by data from old 1990 pumpkins. On or about Oct. 9, 1991, the inventor observed some pumpkins which had been harvested on or before Sep. 10, 1990. From these pumpkins, 17 pumpkins were intact.

When they were grown, the plants that produced these pumpkins were treated with FLOREL according to the previously described method as used for the 1991 crop, except that the concentration was 250–300 parts per million.

TABLE 5

| Line | Diameter In Inches | Height In Inches |
|---|---|---|
| 3 A. | 2 12/16 | 1 10/16 |
| 3 B. | 2 12/16 | 1 10/16 |
| 3 C. | 2 8/16 | 1 12/16 |
| 3 D. | 2 7/16 | 1 8/16 |
| 3 E. | 2 8/16 | 1 9/16 |
| 2 A. | 2 11/16 | 1 10/16 |
| 4 A. | 3 1/16 | 1 13/16 |
| 4 B. | 3 1/16 | 2 1/16 |
| 4 C. | 2 12/16 | 1 13/16 |
| 6 A. | 2 13/16 | 1 12/16 |
| 6 B. | 2 11/16 | 1 10/16 |
| 6 C. | 2 11/16 | 1 8/16 |
| 6 D. | 2 10/16 | 1 7/16 |
| 6 E. | 2 5/16 | 1 7/16 |
| 6 F. | 2 7/16 | 1 7/16 |
| 6 G. | 2 7/16 | 1 8/16 |
| 6 H. | 2 5/16 | 1 5/16 |

The lightest white pumpkins in table 5 corresponded to a whiteness of 158A from fan 4, and the darkest white pumpkins corresponded to the whiteness of 11B from fan 1 of the previously cited color chart of The Royal Horticultural Society.

In sum, the pumpkins of the present invention add to plant diversity; they can be used as ornamentals either alone or in combination with other parts of plants or accents for decorative purposes. The pumpkins of the present invention can also be used in substitute for pumpkins of the prior art as food or in pies.

What is claimed is:

1. A pumpkin having a mass and a weight at maturity the weight being less than 492 grams and having a color of 158A or whiter as measured with reference to fan 4 of The Royal Horticultural Society Colour Chart.

2. The pumpkin of claim 1, wherein the weight is less than 150 grams.

3. The pumpkin of claim 1, wherein the weight is less than 100 grams.

4. The pumpkin of claim 3, wherein the pumpkin has a height in the range of 1 3/16 inches to 1 14/16 inches.

5. The pumpkin of claim 1, wherein the weight is less than 50 grams.

6. The pumpkin of claim 5, wherein the pumpkin has a height in the range of 1 9/16 inches to 2 15/16 inches.

7. The pumpkin of claim 1, wherein the pumpkin is a *Cucurbita pepo*.

8. The pumpkin of claim 1, wherein the pumpkin has a diameter in the range of 2 11/16 inches to 4 4/16 inches.

9. The pumpkin of claim 1, wherein the pumpkin has a diameter in the range of 1 15/16 inches to 2 15/16 inches.

10. The pumpkin of claim 1, wherein the pumpkin has a height in the range of 1 9/16 inches to 2 15/16 inches.

11. The pumpkin of claim 1, wherein the pumpkin has a Connecticut Field shape.

12. The pumpkin of claim 1, wherein the pumpkin is not a Connecticut Field shape, and has a top that is not indented.

13. A plant capable of producing a pumpkin having a mass and weight at maturity of less than 492 grams and having a color of 158A or whiter as measured with reference to fan 4 of The Royal Horticultural Society Colour Chart.

14. A seed capable of germinating into a plant capable of producing a pumpkin having a mass and weight at maturity of less than 492 grams and having a color of 158A or whiter as measured with reference to fan 4 of The Royal Horticultural Society Colour Chart.

15. tissue from a plant producing a pumpkin having a mass and weight at maturity of less than 492 grams and having a color of 158A or whiter as measured with reference to fan 4 of The Royal Horticultural Society Colour Chart.

16. A method for producing a new variety of plant, the method comprising the steps of:

cross-pollinating a plant of a variety capable of producing pumpkins having a mass and weight at maturity of less than 492 grams and having a color of 158A or whiter as measured with reference to fan 4 of The Royal Horticultural Society Colour Chart with another variety of Cucurbitaceae plant to produce fruit with seeds; and germinating the seeds to produce the new variety of plant.

17. The method of claim 16, wherein the step of cross-pollinating another Cucurbitaceae plant is carried out by cross-pollinating with another variety of *Cucurbita pepo*.

18. A plant derived from the variety of plant that produced the seeds deposited with the American Type Culture Collection and assigned deposit account No. 75121.

19. A seed resulting from cross-pollinating a plant capable of producing a pumpkin having a a mass and weight at maturity of less than 492 grams and having a color of 158A or whiter as measured with reference to fan 4 of The Royal Horticultural Society Colour Chart.

20. A seed capable of germinating into a plant capable of producing a pumpkin having a mass and weight at maturity of less than 492 grams and having a color of 158A or whiter as measured with reference to fan 4 of The Royal Horticultural Society Colour Chart.

21. A method for using a plant producing small white pumpkins to produce even smaller white pumpkins, the method comprising the steps of:

germinating seed to produce a plant capable of producing pumpkins of a first size and having a color of 158A or whiter as measured with reference to fan 4 of The Royal Horticultural Society Colour Chart;

applying Ethephon (2-chloroethyl) to said plant prior to the formation of fruit on said plant; and when the fruit reach maturity, harvesting the fruit to obtain white pumpkins having another size smaller than said first size, the pumpkins of said another size having a mass and a weight, the size being less than 2-15/16 inches and the weight being less than 153 grams.

22. A seed deposited with the American Type Culture Collection and assigned deposit No. 75121.

* * * * *